(12) United States Patent
Brown et al.

(10) Patent No.: US 7,416,543 B2
(45) Date of Patent: Aug. 26, 2008

(54) DRAINAGE BAG

(75) Inventors: Malcolm David Brown, Munford (GB); Louise Mulroy, March (GB); Edward Zbygniew Nowak, Impington (GB)

(73) Assignee: Bioprogress Technology International, Inc., Atlanta, GA (US)

( * ) Notice: Subject to any disclaimer, the term of this patent is extended or adjusted under 35 U.S.C. 154(b) by 33 days.

(21) Appl. No.: 10/488,642

(22) PCT Filed: Aug. 30, 2002

(86) PCT No.: PCT/GB02/04005

§ 371 (c)(1),
(2), (4) Date: Mar. 4, 2004

(87) PCT Pub. No.: WO03/020328

PCT Pub. Date: Mar. 13, 2003

(65) Prior Publication Data

US 2005/0004539 A1    Jan. 6, 2005

(30) Foreign Application Priority Data

Sep. 5, 2001    (GB) ................................ 0121422.0

(51) Int. Cl.
*A61F 5/44* (2006.01)
(52) U.S. Cl. .................. 604/332; 604/343; 604/355
(58) Field of Classification Search .......... 604/327, 604/332, 355, 317, 333, 334, 335, 336, 337, 604/343
See application file for complete search history.

(56) References Cited

U.S. PATENT DOCUMENTS 3,089,493 A * 5/1963 Galindo .................. 604/342
3,790,067 A * 2/1974 Scheier ..................... 383/1
3,817,932 A * 6/1974 Albers et al. ............ 528/291
3,886,112 A * 5/1975 Watson et al. ........... 524/388
3,934,587 A * 1/1976 Gordon .................... 604/364
4,136,798 A * 1/1979 Oberstein ................. 383/1
4,416,791 A * 11/1983 Haq ......................... 510/296
4,762,738 A * 8/1988 Keyes et al. ............ 428/34.3
4,772,279 A * 9/1988 Brooks et al. ........... 604/339
4,979,980 A * 12/1990 Thaler et al. ............. 71/64.02

(Continued)

FOREIGN PATENT DOCUMENTS

EP        0272816 A2 *  6/1988

(Continued)

OTHER PUBLICATIONS

Merck Index, 12th Ed., pp. 1308-1309 (1996).*

*Primary Examiner*—T. Zalukaeva
*Assistant Examiner*—Paula L Craig
(74) *Attorney, Agent, or Firm*—McDermott Will & Emery, LLP

(57) ABSTRACT

A drainage bag for receiving bodily waste, such as an ostomy bag, comprises an outer bag of material soluble in cold water, e.g. polyvinyl alcohol, and an inner bag of material insoluble in water at ambient temperature and body temperature but soluble in organic solvent, e.g. 2-oxepanone polymer (polycaprolactone). When the bag (and contents) are to be disposed of, appropriate organic solvent (e.g. benzyl alcohol) is applied to the inner bag. The bag can then be placed in a WC bowl and is flushable after about 1-2 minutes.

8 Claims, 2 Drawing Sheets

U.S. PATENT DOCUMENTS

Figure 1:
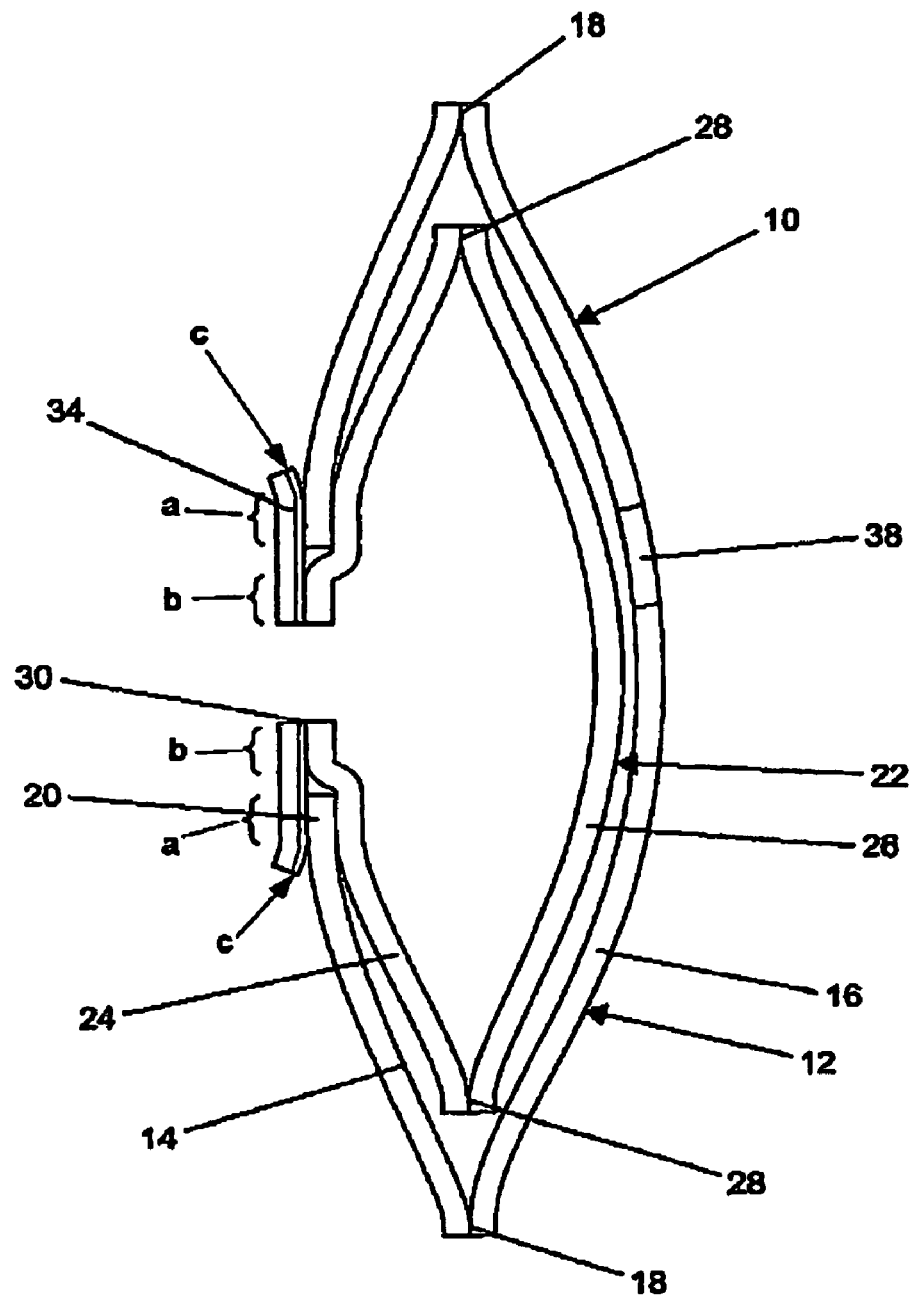

| | | | |
|---|---|---|---|
| 5,009,647 A * | 4/1991 | Cross et al. | 604/332 |
| 5,110,390 A * | 5/1992 | Martini et al. | 156/244.11 |
| 5,244,731 A * | 9/1993 | Saito et al. | 428/372 |
| 5,283,090 A * | 2/1994 | Umemura | 428/35.4 |
| 5,403,299 A * | 4/1995 | Schneider | 604/332 |
| 5,468,526 A * | 11/1995 | Allen et al. | 428/35.4 |
| 5,681,299 A * | 10/1997 | Brown | 604/364 |
| 5,769,831 A * | 6/1998 | Freeman et al. | 604/332 |
| 5,865,819 A * | 2/1999 | Cisko et al. | 604/339 |
| 5,938,647 A * | 8/1999 | Smith | 604/332 |
| 6,211,309 B1 * | 4/2001 | McIntosh et al. | 525/535 |
| 6,217,562 B1 * | 4/2001 | Brown et al. | 604/327 |
| 6,252,027 B1 * | 6/2001 | Mihara et al. | 527/311 |
| 2001/0054567 A1 * | 12/2001 | Desmarais et al. | 206/524.7 |

FOREIGN PATENT DOCUMENTS

| | | | |
|---|---|---|---|
| GB | 2083762 A * | 3/1982 | |
| GB | 2195919 A * | 4/1988 | |
| GB | 233462 A * | 7/1989 | |
| WO | WO 94/12128 * | 6/1994 | |
| WO | WO 96/24317 * | 2/1996 | |

* cited by examiner ical problem for users. This has led to various pro-
DRAINAGE BAG

FIELD OF THE INVENTION

This invention concerns drainage bags for receiving bodily waste, particularly ostomy bags or pouches for receiving waste from colostomy, ileostomy and urostomy patients, urine pouches and the like.

BACKGROUND TO THE INVENTION

Ostomy bags are in widespread use for collecting unabsorbed or excreted bodily waste material from the digestive tracts of colostomy, ileostomy and urostomy patients. Disposal of used ostomy bags and their contents presents a serious practical problem for users. This has led to various proposals for ostomy bags that can be disposed of (with contents) by being flushed down a conventional domestic water closet (WC). Potential problems that arise in this connection include bags floating and failing to flush and bags flushing but causing blockage of drains. Flushable ostomy bags should also ideally be biodegradable, for environmental reasons.

GB 2083762 discloses a WC-disposable ostomy pouch made of composite sheet material comprising an inner layer of mechanically weaker, water-impermeable material, e.g. polyvinylidene chloride (PVDC) and an outer layer of mechanically stronger, water-soluble or disintegratable material, e.g. appropriate grades of polyvinyl alcohol (PVA).

WO 94/12128 discloses an ostomy bag comprising a water-impermeable outer bag, e.g. of polyvinyl chloride (PVC) and a water impermeable inner bag, e.g. of polyvinyl alcohol (PVA) of a grade that is slowly soluble in cold water. The outer and inner bags are detachably secured together such that when the bag has been used and is ready for disposal, the outer bag is detached from the inner bag for separate disposal, e.g. in a domestic household waste bin. The inner bag and contents are removed from the body of a user and can be flushed away down a WC.

Another approach is to provide flushable ostomy bags comprising pH-sensitive material. See, e.g., GB 2195919 and U.S. Pat. No. 5,417,677.

WO 96/37171 discloses other approaches including flushable ostomy pouches comprising water-insoluble but organic solvent-soluble materials.

SUMMARY OF THE INVENTION

The present invention provides a drainage bag for receiving bodily waste, comprising an outer bag of material soluble in cold water (at a temperature in the range 5 to 25° C.) and an inner bag of material insoluble in water at ambient temperature (up to about 40° C.) and body temperature (about 38° C.) but soluble in organic solvent.

In use, the drainage bag is attached to or associated with the body of a user in appropriate manner to receive bodily waste. The inner bag, being of material insoluble in water at ambient temperature (up to about 40° C. depending on climate and other circumstances, typically about 20° C. in a temperate climate) and body temperature (about 38° C.), retains waste received therein. The outer bag provides additional strength and can also provide good odour barrier properties to the drainage bag as a whole. When the drainage bag (and contents) are to be disposed of, the bag is removed from the body of the user. Appropriate organic solvent is applied to the inner bag in a number of possible ways to be discussed below. The bag is placed in a WC bowl and the WC flushed. The inner bag dissolves in the solvent, at least to a sufficient extent to be flushable, and the outer bag dissolves in the water in the WC bowl, at least to a sufficient extent to be flushable, typically within about 1 to 2 minutes, enabling the bag and contents to be flushed away without causing blockage of drains. Any undissolved outer bag material will dissolve completely over time, e.g. over the course of a few days. Any undissolved inner bag material is preferably biodegradable and subject to attack by microbes in sewage treatment works.

The inner bag conveniently comprises 2-oxepanone polymer (also known as polycaprolactone), polyester amide or copolyester having suitable solubility properties. Suitable materials are commercially available, with suitable 2-oxepanone homopolymers including CAPA FB 100 polycaprolactone (CAPA FB 100 is a Trade Mark) from Solvay Caprolactones, Solvay Interox Ltd. Suitable polyester amides include materials known by the Trade Marks BAK 1095 and LP BAK 404-004 from Bayer. The copolyester is conveniently poly(tetramethyleneadipate-co-terephthalate) e.g. in the form of Eastar Bio GP copolyester (Eastar Bio GP is a Trade Mark) from Eastman Chemical Company. The polycaprolactone may be plasticised, e.g. using a citrate ester, to enhance softness. All of these materials also have the advantage of being biodegradable. All of the above materials are insoluble in water at temperatures of up to at least 40° C. but are rapidly soluble at ambient temperature in the organic solvent benzyl alcohol, dissolving substantially completely within 1 to 2 minutes. Benzyl alcohol is a convenient solvent to use, being non-flammable, non-toxic, cheap and readily available. Other possible solvents include toluene, glacial acetic acid and N-methyl pyrrolidone, but these have the respective disadvantages of being highly flammable, corrosive and less effective under water.

The outer bag may be made from a wide range of materials soluble in cold water (i.e. at a temperature of WC flush water (which may vary between about say 5° C. and 25° C. depending on factors including climate, typically being about 15° C. in a temperate climate)), including polyvinyl alcohol (PVA), hydroxypropyl methyl cellulose (HPMC), polyethylene oxide etc. Suitable materials are commercially available. The outer bag is preferably made of biodegradable material; all of the materials listed above are biodegradable. The currently preferred outer bag material is PVA, which is available in a wide range of grades having suitable solubility properties, such as partially hydrolysed grades of PVA with a temperature of dissolution in the range of 5° C. to 30° C. An example of a suitable commercially available PVA is Mono-sol M-7030 (Mono-sol M-7030 is a Trade Mark) from Chris Craft Industrial Products Inc., which has a temperature of dissolution of about 10° C. PVA also has the advantage of having good odour barrier properties. It is further preferred to use a film of PVA coated with or incorporating alginate or gelatin, to improve odour barrier properties. Such a coating is provided on one face only of the film material, forming the outwardly facing face of the bag. The coating conveniently comprises two layers, a tie coat and a top coat.

The odour barrier properties of the outer bag material may be further enhanced by including in or on the material odour-absorbing material, e.g. in the form of clay particles such as nanoclay materials available from Nanocor Inc.

The organic solvent may be applied to the inner bag in a number of ways, including those disclosed in WO 96/37171. These include providing a container, e.g. sachet, containing a suitable dose of solvent (e.g. about 0.5 ml) within the inner bag or between the inner and outer bags, the container being rupturable, e.g. by application of external force, to release the solvent contents and thus result in the solvent contacting the inner bag. As a further possibility, the drainage bag may be provided with a valved inlet leading from the exterior to either the interior of the inner bag or the space between the inner and outer bags, enabling solvent to be introduced and so brought into contact with the inner bag. To this end, the user may be provided with a container of solvent, e.g., a pressurised spray or pump action device, possibly designed to delivery a metered dose of suitable size of the solvent, e.g. 3 or 4 sprays of solvent, amounting to a total of about 0.5 ml. Another possibility is for the outer bag to include a removable portion, e.g. a tear-off panel, for removal by a user, to expose the inner bag. Alternatively, a portion of the outer bag may be penetrated, e.g. by use of a pierce point provided to the user. The user then applies solvent to the inner bag, e.g. from a container as discussed immediately above.

The bag may thus be sold together with a supply of appropriate solvent, with the solvent preferably dispensable in metered doses of appropriate size.

The drainage bag is typically embodied as an ostomy bag. In this case, the bag includes suitable means for attaching the bag to the body of a user. Such means typically comprise an annular flange or wafer on the exterior of the bag, surrounding respective inlet apertures in the outer and inner bags through which bodily waste can pass to be collected in the inner bag. The inlet aperture in the outer bag is preferably larger than the inlet aperture in the inner bag, with the flange attached to annular portions of both the inner and outer bag walls. In this way the flange acts to protect the outer bag (which is made of cold water-soluble material) from contact with the bag contents in normal use. The flange conveniently functions to secure the inner and outer bags together. The flange is suitably made of hydrocolloid material, e.g. carboxymethylcellulose or polyisobutylene or mixtures of these materials. The hydrocolloid flange material functions as an adhesive, enabling adhesion to the skin of a user. The inner surface of the flange (for attachment to the baa wall) may be laminated to a film of material soluble under the same conditions as either the outer bag material (ie soluble in cold water) or the inner bag material (ie insoluble in water at ambient temperature and body temperature but soluble in organic solvent). The laminate film material is preferably biodegradable, and is preferably polycaprolactone, polyvinyl alcohol or polyurethane. The laminate film material is preferably also attached directly to the bag wall material, eg using a suitable adhesive or by heat sealing. For example, where the flange is laminated to a film of polycaprolactone, a heat seal can be used to attach the polycaprolactone to the inner bag material and adhesive can be used to attach the polycaprolactone to the outer bag material. Where the flange is laminated to a film of polyvinyl alcohol, adhesive can be used to attach the polyvinyl alcohol to the inner bag material and heat sealing can be used to attach the polyvinyl alcohol to the outer bar material.

The means for attaching the bag to the body of a user may alternatively comprise a two-part body attachment, including a base portion semi-permanently mounted around the abdominal opening of a user, with the flange or wafer of the bag sealingly engaging in known manner with the base portion.

The drainage bag conveniently includes a gas valve to permit escape of flatus gases from the bag. The valve may have an associated odour filter, in known manner.

The drainage bag desirably has on at least the surface thereof adjacent the body of a user, in use, a layer of soft material (known as a comfort panel) e.g. of woven viscose or cotton bonded by water dispersible PVA.

Figure 2:
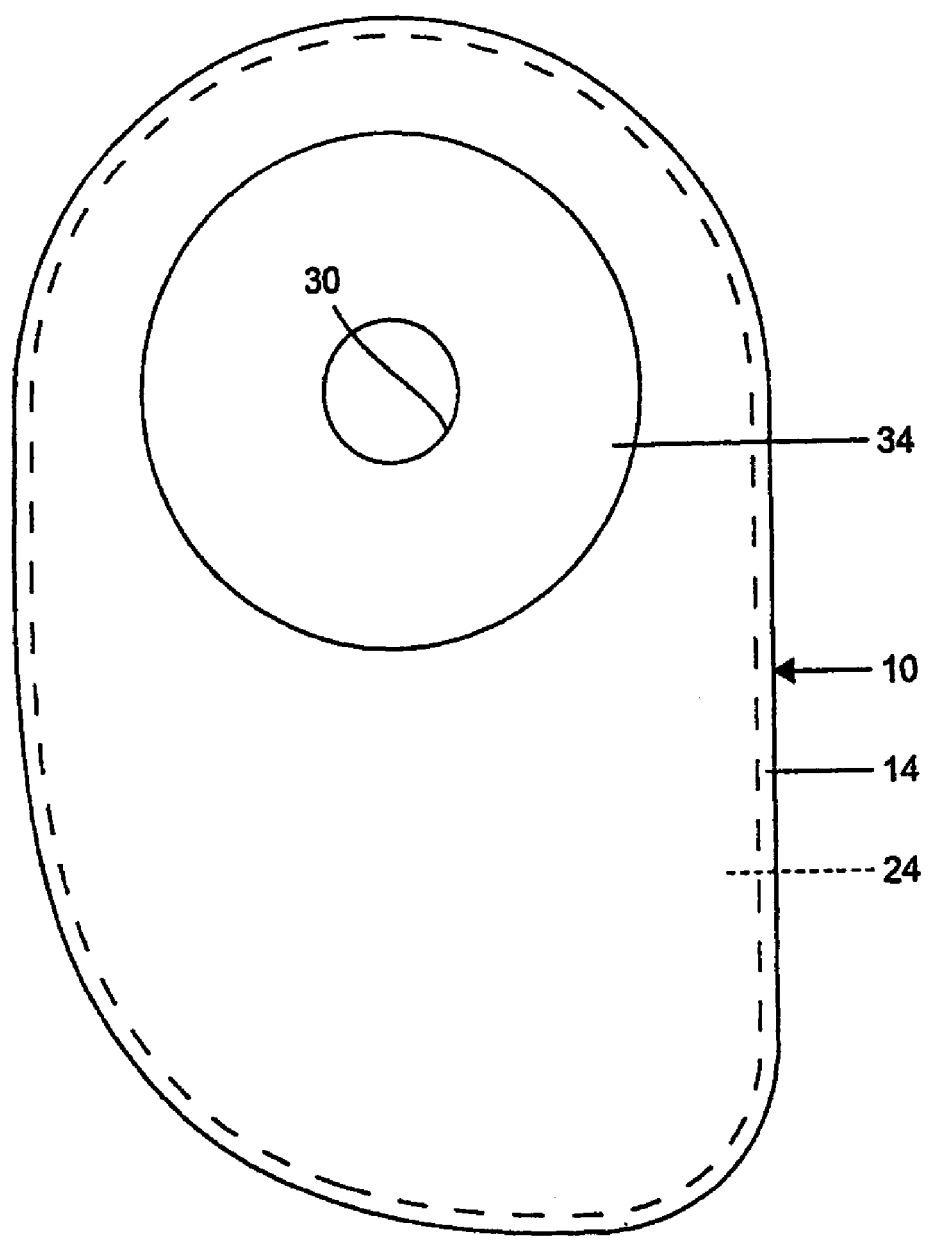

The invention will be further described, by way of illustration, with reference to the accompanying drawings, in which:

FIG. 1 is a schematic sectional view of one embodiment of an ostomy bag in accordance with the invention; and FIG. 2 is a front view of the bag of FIG. 1 on a larger scale.

Referring to the drawings, the illustrated ostomy bag 10 comprises an outer bag 12 having a front panel 14 and a rear panel 16. Panels 14 and 16 each comprise a film of Mono-sol M-7030 cold water-soluble PVA 75 μm thick, coated with alginate on one face thereof (which forms the outer face of the bag). The coating comprises two layers, as follows:

1) A tie coat applied at 10 gsm.

The dried tie coat consists of the following percentage by weight solids

| | |
|---|---|
| 49.7% | Polyvinyl alcohol |
| 29.0% | Sodium alginate |
| 20.5% | Glycerin |
| 0.8% | Preservative, i.e. 2-bromo-2-nitropropane-1,3-diol |

2) A top coat applied at 50 gsm

The dried top coat consists of the following percentage by weight solids:

| | |
|---|---|
| 66.0% | Sodium alginate |
| 33.0% | Glycerin |
| 1.0% | Preservative, i.e. 2-bromo-2-nitropropane-1,3-diol |

The two panels 14 and 16 are secured together by heat sealing around their periphery, as shown at 18, to form a bag. The front panel 14 includes a circular opening 20, constituting an inlet to the bag.

The bag 10 further comprises an inner bag 22 having a front panel 24 and a rear panel 26. Panels 24 and 26 each comprise a film of CAPA FB 100 polycaprolactone 25 μm thick secured together by heat sealing around their periphery, as shown at 28, to form a bag. The front panel 24 includes a circular opening 30, constituting an inlet to the bag.

The circular opening 20 of the outer bag has a larger diameter than the circular opening 30 of the inner bag. This is to protect the water-soluble film of the outer bag from excreted bodily waste. The inner and outer bags are not physically attached directly to each other. A flange or wafer 34 of hydrocolloid material (a mixture of carboxymethylcellulose and polyisobutylene) with a polycaprolactone backing layer "c" laminated thereto is secured to the outer face of panel 14 and panel 24 in the areas labeled "a" and "b" respectively, thus functioning sealingly to secure the inner and outer bags together. The wafer backing layer "c" of polycaprolactone is attached to panel 14 by use of a suitable adhesive and is attached to panel 24 by use of heat sealing.

A layer of woven viscose material (not shown), constituting a comfort panel, is provided on the outer surface of front panel 14, surrounding flange 34, and on the outer surface of rear panel 16.

The rear panel 16 of the outer bag includes a removable portion, represented at 38.

The bag has an overall length of about 205 mm and an overall with of about 145 mm, with a maximum capacity of 250 ml to 300 ml.

In use, the bag 10 is fitted to the body of a user by adhering flange 34 to the abdomen of a user, surrounding the abdominal opening. Unabsorbed or excreted bodily waste passes into the bag 10 through openings 20 and 30 and collects in the inner bag 22.

When the bag 10 is to be disposed of, the bag is removed from the body of the user. The comfort panel is removed either with a pull strip or by means of a large overlapped split in the comfort panel on the rear panel 16 that allows access to the rear face of the bag (remote from the body in use). Portion 38 of rear panel 16 is removed, e.g. by tearing with the assistance of a peel back tab (not shown), and an appropriate dose (about 0.5 ml) of benzyl alcohol applied to the surface of the inner bag 22, by spraying from a container (not shown). The bag is placed in a WC bowl, where the comfort panel disperses and the outer bag starts to dissolve in the water in the WC bowl and the inner bag dissolves in the applied benzyl alcohol, allowing the bag contents to escape into the WC bowl. After a minute or so, the bag is sufficiently dissolved to be in flushable condition, along with the bag contents, and can be disposed of by flushing the WC.

The invention claimed is:

1. A drainage bag for receiving bodily waste, comprising:
an outer bag
an inner bag; and
a pouch or sachet containing an organic solvent;
wherein: the outer bag is made of material soluble in cold water;
the inner bag is made of material insoluble in water at ambient temperature and body temperature but rapidly soluble at ambient temperature in the organic solvent;
the outer bag is separate from the inner bag;
the material of the outer bag is different from the material of the inner bag;
inner bag comprises a material, the material being selected from the group consisting of 2-oxepanone polymer (polycaprolactone), polyester amide and copolyester;
the outer bag comprises a material, the material being selected from the group consisting of polyvinyl alcohol, hydroxypropyl methyl cellulose and polyethylene oxide; and
the organic solvent is benzyl alcohol.

2. A drainage bag according to claim 1, wherein the outer bag comprises polyvinyl alcohol coated with or incorporating alginate or gelatin.

3. A drainage bag according to claim 1, wherein the inner bag comprises 2-oxepanone polymer (polycaprolactone) and the outer bag comprises polyvinyl alcohol.

4. A drainage bag according to claim 1, further comprising a flange for attachment to the body of a user and secured with respect to the inner and outer bags, surrounding respective inlet apertures therein.

5. A drainage bag according to claim 4, wherein a layer of film material soluble under the same conditions as either the outer bag material or the inner bag material is laminated to the surface of the flange remote from the body of a user, in use.

6. A drainage bag according to claim 5, wherein the laminated film material is selected from the group consisting of 2-oxepanone polymer (polycaprolactone), polyvinyl alcohol and polyurethane.

7. A drainage bag according to claim 5, wherein the laminated film material is attached directly to the bag wall material.

8. A drainage bag according to claim 4, wherein the inlet aperture in the outer bag is larger than the inlet aperture in the inner bag.

* * * * *